United States Patent
Hui et al.

(10) Patent No.: US 10,475,355 B2
(45) Date of Patent: Nov. 12, 2019

(54) METHOD OF PROVIDING MARKINGS TO PRECIOUS STONES INCLUDING GEMSTONES AND DIAMONDS, AND MARKINGS AND MARKED PRECIOUS STONES MARKED ACCORDING TO SUCH A METHOD

(71) Applicant: Master Dynamic Limited, Shatin, New Territories (HK)

(72) Inventors: Koon Chung Hui, Hong Kong (HK); Wing Chi Tang, Kowloon (HK); Ho Ching, Kowloon (HK)

(73) Assignee: Chow Tai Fook Jewellery Company Limited, Hong Kong (HK)

( * ) Notice: Subject to any disclaimer, the term of this patent is extended or adjusted under 35 U.S.C. 154(b) by 589 days.

(21) Appl. No.: 14/286,306

(22) Filed: May 23, 2014

(65) Prior Publication Data
US 2015/0101365 A1    Apr. 16, 2015

(30) Foreign Application Priority Data

Oct. 11, 2013 (HK) .................................... 13111497
Mar. 10, 2014 (HK) .................................... 14102399

(51) Int. Cl.
*G09F 3/00* (2006.01)
*A44C 17/00* (2006.01)
(Continued)

(52) U.S. Cl.
CPC ................ *G09F 3/00* (2013.01); *A44C 17/00* (2013.01); *B23K 26/0006* (2013.01);
(Continued)

(58) Field of Classification Search
CPC ..... A44C 17/00; A44C 17/001; A44C 17/005; G01N 21/87; G02B 5/18; G02B 5/1857;
(Continued)

(56) References Cited

U.S. PATENT DOCUMENTS 4,184,079 A   1/1980   Hudson et al.
4,467,172 A   8/1984   Ehrenwald et al.
(Continued)

FOREIGN PATENT DOCUMENTS

CN   1896315 A      1/2007
CN   101142598 A    3/2008
(Continued)

OTHER PUBLICATIONS

UKIPO, Search Report in connection with related Hong Kong Patent App. No. 13111497.0, dated Oct. 29, 2013, 2 pages.
(Continued)

*Primary Examiner* — Catherine A. Simone
(74) *Attorney, Agent, or Firm* — Kolisch Hartwell, P.C.

(57) ABSTRACT

An identifiable mark on a portion of a polished facet of a surface of an article and being identifiable by an optical magnifying viewing device, the identifiable mark comprising a nano-structure formed by a two-dimensional or a three-dimensional lattice of a plurality of discrete nanometer sized recessed or protruded entities, wherein the entities are arranged within a predefined region of the polished facet in a predetermined arrangement in relation to each other. The predetermined arrangement of the entities is non-uniform and non-periodic arrangement, and wherein the entities are sized and shaped so as to cause optical scattering upon reflection of incident light having one or more predetermined wavelengths by the lattice at a predetermined angle of incidence to the lattice and the distance from the inner interface surface to the outer interface surface is greater than the amplitude of the non-marked portion of the polished face.

15 Claims, 14 Drawing Sheets

(51) Int. Cl.
| | |
|---|---|
| *B41M 5/24* | (2006.01) |
| *G02B 5/18* | (2006.01) |
| *B23K 26/00* | (2014.01) |
| *B23K 26/352* | (2014.01) |
| *G01J 1/08* | (2006.01) |
| *G09F 23/00* | (2006.01) |
| *G01N 21/87* | (2006.01) |
| *B23K 103/00* | (2006.01) |

(52) U.S. Cl.
CPC ............ *B23K 26/355* (2018.08); *B41M 5/24* (2013.01); *G01J 1/08* (2013.01); *G02B 5/1842* (2013.01); *G02B 5/1857* (2013.01); *G02B 5/1861* (2013.01); *G09F 23/00* (2013.01); *B23K 2103/50* (2018.08); *G01N 21/87* (2013.01)

(58) Field of Classification Search
CPC ...... G02B 5/1842; G02B 5/1861; B44B 7/00; B44B 7/002; C23C 14/46; G06K 9/00577; G06K 19/0614; G06K 19/06178; B41M 5/26; B41M 5/262; B41M 5/24; B44C 1/228; G09F 3/00; B44F 1/10; B23K 26/355
See application file for complete search history.

(56) References Cited

U.S. PATENT DOCUMENTS

| | | | |
|---|---|---|---|
| 5,702,586 A | 12/1997 | Pehrsson et al. | |
| 5,753,887 A | 5/1998 | Rosenwasser et al. | |
| 6,391,215 B1 | 5/2002 | Smith et al. | |
| 8,033,136 B2 | 10/2011 | Maltezos et al. | |
| 9,659,360 B2 * | 5/2017 | Hofsaess ................ | G06T 7/001 |
| 9,901,895 B2 | 2/2018 | Hui et al. | |
| 2004/0067346 A1 | 4/2004 | Hofmann et al. | |
| 2006/0144821 A1* | 7/2006 | Wang .................. | A44C 17/005 |
| | | | 216/66 |
| 2006/0196858 A1 | 9/2006 | Barron et al. | |
| 2007/0109529 A1 | 5/2007 | Wagner et al. | |
| 2009/0122412 A1 | 5/2009 | Steenblik et al. | |
| 2010/0294930 A1 | 11/2010 | Preikszas et al. | |
| 2011/0189446 A1 | 8/2011 | Cross et al. | |
| 2012/0024010 A1 | 2/2012 | Maltezos et al. | |
| 2012/0264237 A1 | 10/2012 | Sheam et al. | |

FOREIGN PATENT DOCUMENTS

| | | |
|---|---|---|
| CN | 101456534 A | 6/2009 |
| EP | 0675324 A1 | 10/1995 |
| EP | 0648445 B1 | 4/1999 |
| EP | 1391841 A1 | 2/2004 |
| EP | 2144117 A1 | 1/2010 |
| GB | 2047215 A | 11/1980 |
| GB | 2248575 A | 4/1992 |
| GB | 2332651 A | 6/1999 |
| WO | 9209876 A2 | 6/1992 |
| WO | 2008008635 A2 | 1/2008 |
| WO | 2010128890 A1 | 11/2010 |

OTHER PUBLICATIONS

UKIPO, Search Report in connection with related Hong Kong Patent App. No. 14102399.7, dated Mar. 20, 2014, 2 pages.

European Patent Office, "Extended European Search Report" in connection with related European Patent Application No. 141695030.1, dated May 21, 2015, 9 pages.

European Patent Office, "European Search Report" in connection with related European Patent Application No. 14169503.1, dated Jan. 13, 2015, 6 pages.

Wei Zhou, Authorized Officer, State Intellectual Property Office of the P.R. China, "International Search Report" in connection with related PCT Patent App. No. PCT/CN2014/078135, dated Aug. 22, 2014, 9 pages.

Wei Zhou, Authorized Officer, State Intellectual Property Office of the P.R. China, "Written Opinion of the International Searching Authority" in connection with related PCT Patent App. No. PCT/CN2014/078135, dated Aug. 22, 2014, 6 pages.

Carter, G. et al., "An STM Study of Atomically-Flat Gold Surfaces Irradiated with Energetic Helium and Argon Ions", Ninth International Conference on ion beam modification of materials, Feb. 5-10, 1995, vol. 28, No. 24, p. 07.017.

The Rayleight Criterion, via http://hyperphysics.phy-astr.gsu.edu/hbase/phyopt/Raylei.html, no date available, 3 pgs.

Was, Gary S., "10.5 Solid Phases and Inert Gas Bubble Lattices", Fundamentals of Radiation Materials Science: Metals and Alloys, Jul. 14, 2007, pp. 535-537.

Wikipedia, "Order of Magnitude" via https://en.wikipedia.org/wiki/Order_of_magnitude, No date available, 8 pgs.

* cited by examiner

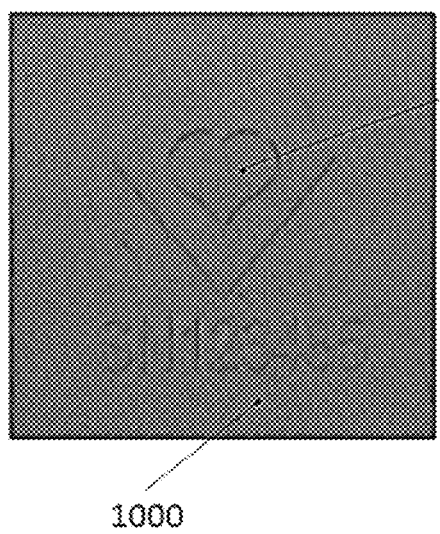
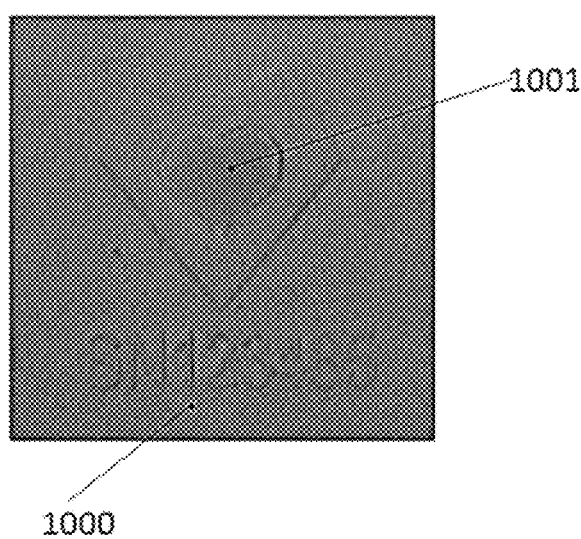
Figure 10A
Figure 10B

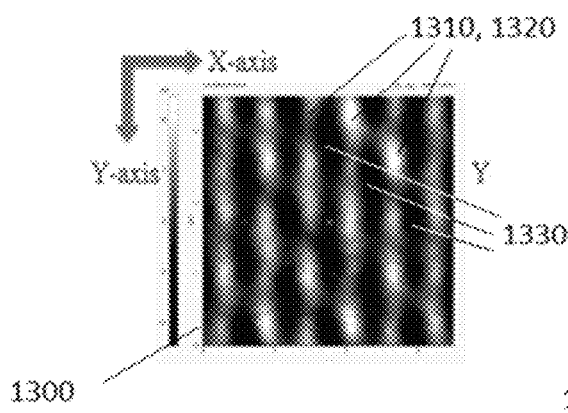
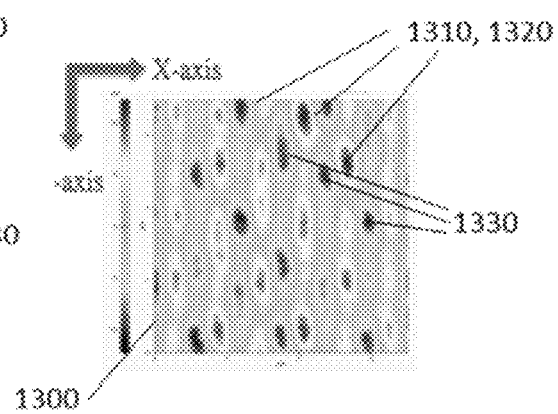
Figure 13A  Figure 13B
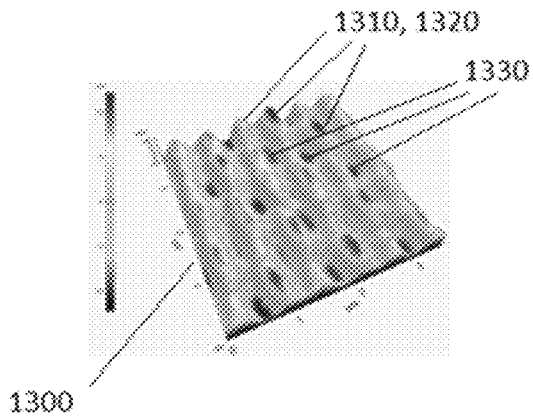
Figure 13C

METHOD OF PROVIDING MARKINGS TO PRECIOUS STONES INCLUDING GEMSTONES AND DIAMONDS, AND MARKINGS AND MARKED PRECIOUS STONES MARKED ACCORDING TO SUCH A METHOD

FIELD OF THE INVENTION

The present invention relates to solid state articles including gemstones and jewelry, and more particularly the marking thereof.

BACKGROUND TO THE INVENTION

In gemstone identification and diamond quality grading and analysis, observation and evaluation from a top view normal to the top surface of gemstone or diamond provides relevant evidence and information pertaining to clarity and cut as certified in reports by international standards laboratories including GIA (Gemological Institute of America Inc.), IGI (International Gemological Institute), Gem-A (The Gemological Association of Great Britain), NGTC (National Gemstone Testing Center, China) and the like.

From a customer standpoint, parameters such as for a diamond, a flashing brightness often utilizing termed such as "brilliance" (the total amount of light that is reflected by a diamond) or "fire" (the dispersion of light into different colours of light), which are typically observed or admired from a top surface as well as from the top table of a diamond, may be utilised.

It is important parameters of gemstones or diamonds, such as those indicative of the quality, grade, cut, origin, be associated with a gemstone or diamond, for both commercial and security purposes.

Within the market, there exist several manners in which a gemstone or diamond may be marked, including for example the Forevermark™, which is mark or inscription on a gemstone or diamond.

However, when observing a gemstone or diamond marked as such utilizing a conventional microscope or loupe and under normal room light condition, such marks affect the brilliance or fire of a diamond

OBJECT OF THE INVENTION

It is an object of the present invention to provide a method of marking of a solid state article, including a gemstone or diamond, which at least ameliorates at least some of the deficiencies as associated with those of the prior art.

SUMMARY OF THE INVENTION

In a first aspect, the present invention provides an identifiable mark on a portion of a polished facet of a surface of an article and being identifiable by an optical magnifying viewing device, said identifiable mark comprising a nano-structure formed by a two-dimensional or a three-dimensional lattice of a plurality of discrete nanometer sized recessed or protruded entities, wherein said entities are arranged within a predefined region of said polished facet in a predetermined arrangement in relation to each other and such that an outer interface surface between the facet of the article and air is formed and an inner interface surface between the facet of the article and air is formed; wherein said predetermined arrangement of said entities is non-uniform and non-periodic arrangement, and wherein said entities are sized and shaped so as to cause optical scattering upon reflection of incident light and the distance from the inner interface surface to the outer interface surface is greater than the amplitude of the non-marked portion of said facet polished facet; such that upon reflection of incident light having one or more predetermined wavelengths by said lattice at a predetermined angle of incidence to said lattice, interference due to scattering of light from said lattice is induced such that said reflected light has a variation in intensity providing one or more local maxima of one or more wavelengths; and said mark is identifiable by way of an optical magnifying viewing device inclined at a requisite viewing angle such that a local maxima is detected.

The two-dimensional or a three-dimensional lattice of nanometer sized discrete entities is preferably formed from a nano-fabrication method. The nano-fabrication method may include focused ion beam, a deep UV (ultraviolet) laser beam, wet chemical etching, ion plasma etching, different aspect ratio of shadow mask for plasma etch process or the like, or any combination thereof.

In an embodiment of the invention, the two-dimensional or a three-dimensional lattice may be formed by a focused ion beam and by way of dynamic control variation of the spot size and dose of the focused ion beam.

Preferably, the entities of said lattice are spaced apart in the range of from 10 nm to 900 nm, the discrete entities have a maximum lateral dimension in the range of from 1 nm to 899 nm, and the normal distance between the outer interface surface and the inner interface surface is in the range of from 1 nm to 200 nm.

The two-dimensional or a three-dimensional lattice preferably provides at least one identifiable mark having two or more colour features viewable by way of said optical magnification viewing device.

Preferably, the requisite viewing angle of said optical magnifying viewing device is in a direction of from normal to said polished facet.

The lattice is preferably provided in a region of about 400 μm×400 μm, and the non-marked portion of said facet preferably has an average surface roughness less than about 1 nm.

Preferably, the ratio of the intensity of said one or more local maxima to that of any reflected signal from the non-marked portion of said facet is greater than a value of order of magnitude of $10^2$.

Preferably, the ratio of the intensity of said one or more local maxima to that of any reflected signal from the non-marked portion of said facet is greater than a value of order of magnitude of up to $10^3$.

The mark is viewable preferably by way of magnification greater than 10× magnification.

Preferably, the variation in intensity is distinguishable by human eye or an optical camera from any reflected signal from the non-marked portion of said facet.

The recessed or protruded entities of said two-dimensional or a three-dimensional lattice may be either regular or irregular shaped holes, dots, disks, pillars or the like.

The nanometer sized discrete entities may be provided as a circular arranged lattice, spiral arranged lattice, square arranged lattice, triangular arranged lattice, hexagonal arranged lattice, fractal arranged lattice, or multiple combination thereof.

Preferably, the local maxima having variation in intensity due to diffracted light is +/−1st order, +/−2nd order, or +/−3rd order light from diffraction of incident light.

The incident light is incident light may be monochromatic or panchromatic, and may a plurality of wavelengths. Preferably, the incident light is collimated and coherent light.

Preferably, the combination of single or multiple wavelength monochromatic light incident at individual specified angles (θ) form a mark combined with different colour as a brand or quality mark.

The mark is preferably on a polished facet of a gemstone, and the gemstone may be selected from the group including Diamond, Ruby, Sapphire, Emerald, Pearl, Jade, Tourmaline or the like.

In a second aspect, the present invention provides an article having thereon an identifiable mark according to the first aspect.

Preferably, the article is a gemstone, and may be selected from the group including Diamond, Ruby, Sapphire, Emerald, Pearl, Jade, Tourmaline or the like.

In a third aspect, the present invention provides a method of providing the identifiable mark on a portion of a polished facet of a surface of an article being identifiable by an optical magnifying viewing device, said method including the steps of forming a nano-structure of a two-dimensional or a three-dimensional lattice of a plurality of discrete nanometer sized recessed or protruded entities on a portion of a facet of an article, wherein said entities are arranged within a predefined region of said facet in a predetermined arrangement in relation to each other, and such that an outer interface surface between the facet of the article and air is formed and an inner interface surface between the facet of the article and air is formed; wherein said predetermined arrangement of said entities is non-uniform and non-periodic arrangement; wherein said entities are sized and shaped so as to cause optical scattering such that upon reflection of incident light, and the distance from the inner interface surface to the outer interface surface is greater than the amplitude of the non-marked portion of said facet polished facet; such that upon reflection of incident light having one or more predetermined wavelengths by said lattice at a predetermined angle of incidence to said lattice, interference due to scattering of light from said lattice is induced such that said reflected light has a variation in intensity providing one or more local maxima of one or more wavelengths; and wherein said mark is identifiable by way of an optical magnifying viewing device inclined at a requisite viewing angle such that a local maxima is detected.

The two-dimensional or a three-dimensional lattice of nanometer sized discrete entities may be formed from a nano-fabrication method, and the nano-fabrication method may include focused ion beam, a deep UV (ultraviolet) laser beam, wet chemical etching, ion plasma etching, different aspect ratio of shadow mask for plasma etch process or the like, or any combination thereof.

In an embodiment of the present invention, the two-dimensional or a three-dimensional lattice may be formed by a focused ion beam and by way of dynamic control variation of the spot size and dose of the focused ion beam.

Preferably, the entities of the lattice are spaced apart in the range of from 10 nm to 900 nm, the discrete entities have a maximum lateral dimension in the range of from 1 nm to 899 nm, and the normal distance between the outer interface surface and the inner interface surface is in the range of from 1 nm to 200 nm.

In an embodiment of the present invention, the two-dimensional or a three-dimensional lattice provides at least one identifiable mark having two or more colour features viewable by way of said optical magnification viewing device.

Preferably, the lattice is provided in a region of about 400 μm×400 μm.

The recessed or protruded entities of said two-dimensional or a three-dimensional lattice may be either regular or irregular shaped holes, dots, disks, pillars or the like, and may be provide as a circular lattice, spiral lattice, square lattice, triangular lattice, hexagonal lattice, fractal lattice or multiple combination thereof.

Preferably, the article is a gemstone, and me be selected from the group including Diamond, Ruby, Sapphire, Emerald, Pearl, Jade, Tourmaline or the like.

In a fourth aspect, the present invention provides an article having an identifiable mark formed on a portion of a polished facet of a surface of the article, wherein the identifiable mark is formed from the method according to the third aspect.

In a further aspect, the present invention provides a method of viewing an identifiable mark on an article according to the fourth aspect, said method including the steps of providing incident light having one or more predetermined wavelengths at a predetermined angle of incidence to the identifiable mark; and viewing said identifiable mark at said requisite viewing angle by way of an optical viewing device such that a local maxima is detected.

In another aspect, the present invention provides a system for viewing an identifiable mark on an article according to the fourth aspect, said system comprising a light source for incident light having one or more predetermined wavelengths at a predetermined angle of incidence to the identifiable mark; and a viewing device for viewing said identifiable mark at said requisite viewing angle by way of an optical viewing device such that a local maxima is detected.

BRIEF DESCRIPTION OF THE DRAWINGS

Embodiments and particulars of the present invention will now be described by way of example only and with reference to the accompanying drawings, whereby:

FIGS. 1 to 9 provide general background and general explanation of light diffraction properties as utilised in accordance with the present invention which are described by way of theoretical and technical explanation as well as theoretic experimental results which demonstrate the use of such diffractive properties, and FIGS. 10 to 14 depict and describe examples of the present invention by way of use of a lattice of entities in a non-uniform and non-periodic arrangement which provide an identifiable mark to a solid state material and explanation thereof is provided, in which:

FIG. 1 is a schematic representation of a cross-sectional view of an array of nano-holes or nano-dots providing theoretical background and general explanation thereof of light diffraction properties as utilised in accordance with the present invention;

FIG. 2 depicts an SEM (scanning electron microscopy) image of nano-holes at a magnification of 7,150×

FIG. 3 depicts an SEM (scanning electron microscopy) image of nano-holes at a magnification of 80,000×;

FIG. 5 is a graph depicting the dependency of the incident launch angle for monochromatic incident light with different wavelengths on periodicity of an array of nano-holes or nano-dots at gemstone-to-air or diamond-to-air interface when observing a mark at an optical axis normal to the facet with the mark;

FIG. 6 is a graph depicting the dependency of the calculated diffraction efficiency for monochromatic incident light with different wavelengths on periodicity of an array of nano-holes or nano-dots at gemstone-to-air or diamond-to-air interface when observing a mark at an optical axis normal to the facet with the mark;

FIG. 7 is a graph depicting the calculated diffraction efficiency and incident launch angle for monochromatic incident light which depends on wavelength of monochromatic incident light when observing a mark at optical axis normal to the facet with the mark;

FIG. 8 is a graph showing that the calculated diffraction efficiency depends on physical depth of an array of nano-holes or nano-dots at gemstone-to-air interface for gemstones with different refractive index when observing a mark at an optical axis normal to the facet with the mark;

FIG. 9 is a graph depicting the On-Off Ratio contrast of the significantly increased and enhanced brightness colour mark comparing to surrounding untreated surface roughness against physical depth of an array of nano-holes or nano-dots at gemstone-to-air interface when observing a mark at an optical axis normal to the facet with the mark;

FIG. 10A is an exemplary photographic representation of an example of a gemstone facet surface marking in accordance with the present invention with a significantly increased and enhanced brightness colour mark having a lattice of entities in a non-uniform and non-periodic arrangement viewed at optical axis normal to the facet with normal white light (left) as an Off-state;

FIG. 10B depicts the gemstone facet surface of the gemstone facet surface of FIG. 10A with normal white light plus intense green monochromatic light simultaneously (right) as an On-state, in accordance with the present invention;

FIG. 11 is a photographic representation of a gemstone facet surface marking in accordance with the present invention of a bi-colour mark having a lattice of entities in a non-uniform and non-periodic arrangement, viewed at optical axis normal to the facet with normal white light plus intense green and red monochromatic light simultaneously as On-state;

FIG. 12 C is an AFM scan of a ROI (Region of Interest) of at middle of the concerned triangle colour mark according to the present invention as shown in FIG. 12B showing a lattice of irregular/non-periodic spaced entities;

FIG. 13A is the detailed AFM scan similar to that of as FIG. 12D showing the lattice of irregular/non-periodic spaced entities with arbitrary spacing and shapes as same with X-Y axis shown at the left-upper corner according to the present invention;

FIG. 13B is a colour transformed AFM scan of FIG. 13A with rainbow colour range from Blue to Red to represent topographic change from lowest depth (Blue) to top surface (Red) as well as clearly showing the construction of arbitrary shapes having a lattice irregular/non-periodic spaced entities in both X-axis and Y-axis according to the present invention;

FIG. 13C is a 3D contour plot of FIG. 13B depicted change of topography due to arbitrary shaped and lattice of irregular/non-periodic spaced entities according to the present invention; and FIG. 14 is a schematic representation of a focused ion beam pass across top surface of gemstone facet to fabricate entities along the Y-axis with various spacings and Z-axis having various depths according to the present invention.

DETAILED DESCRIPTION OF THE CERTAIN PREFERRED EMBODIMENT

Figure 1:
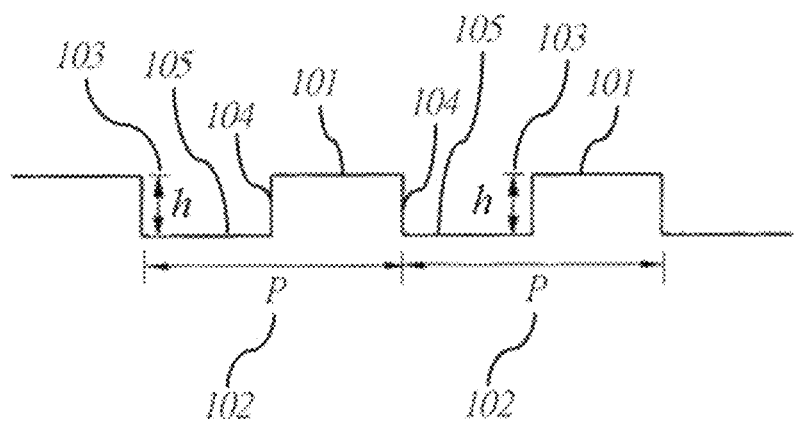

The present invention pertains to an information marking applied to solid state materials including gemstone, including Diamond, Ruby, Sapphire, Emerald, Pearl, Jade, Tourmaline and the like, and other such solid state materials such as silicon, which is may be applied to such a solid state material such as to a polished facet of a gemstone and which is invisible to the naked eye and is invisible when utilizing a typical camera equipped microscope under normal light conditions.

The invention is implemented by forming a mark with depth in the nanometer range by way of high energy beams or reactive ion etch, in a manner without affecting the clarity grade and brilliance or fire of the gemstone or diamond.

The mark may be any mark or character, and may be implemented in a manner so as not to detract from the value or appearance of a solid state material such as a gemstone or diamond, and should preferably not exhibit blackening, as gemstones and diamonds are often prized for their optical properties and rarity and perceived beauty.

The manner in which the present invention is realized is by application of optical diffraction properties in a lattice of nanometer sized periodic structure within the scale of nanometers shallow depth in marking a surface of a gemstone. Such diffractive properties induce interference in relation to reflected light such that the reflected light has a variation in intensity providing one or more local maxima. This allows for the application of an identification mark, which is invisible to naked eye under normal light illumination, whereby the mark may be applied to a solid state material such as a polished facet of a gemstone by way of nano-fabrication technologies such as focused energy beams or reactive ion etch, without detracting from its clarity or colour grade of the gemstone.

Due to Rayleigh Criterion in optical limit, single or randomly arranged of few hundreds nanometer sized structure with few nanometers in depth cannot be recognized optically under visible light range even by high magnification optical microscope.

Thus, the present invention of a normally optically invisible marking in a lattice of nanometer sized periodic structure can be viewed under specified predetermined conditions, yet is invisible under visible light range.

The present invention, by use of focused ion beam to provide the marking, allows a marking structure on a solid state material formed from a two-dimensional or a three-dimensional lattice of discrete entities, whereby the entities are in a non-periodic and non-symmetric arrangement.

The present invention, by way of such a non-periodic and non-symmetric arrangement of entities allows for more complex marking as those of the prior art, as well as more than one colour of light to be reflected readily from the same single marking. Furthermore, the use of the present invention allows for a marking structure for which the size, shape, geometry and spacing may be varied, thus allowing for more complex marking as well as a plurality of colour components to be viewable.

With reference to FIGS. 1 to 9, by way of theoretical background and general explanation thereof of light diffraction properties as utilised in accordance with the present invention are described by way of theoretical and technical explanation as well as theoretic experimental results which demonstrate the use of such diffractive properties. Although these figures show a regular array formation of entities, this is for explanatory purposes, and is not a limitation of the present invention.

With reference to FIGS. 10 to 14, examples of the present invention by way of use of a lattice of entities in a non-periodic and non-symmetric arrangement which provide an identifiable mark to a solid state material and explanation thereof is provided.

Figure 2:
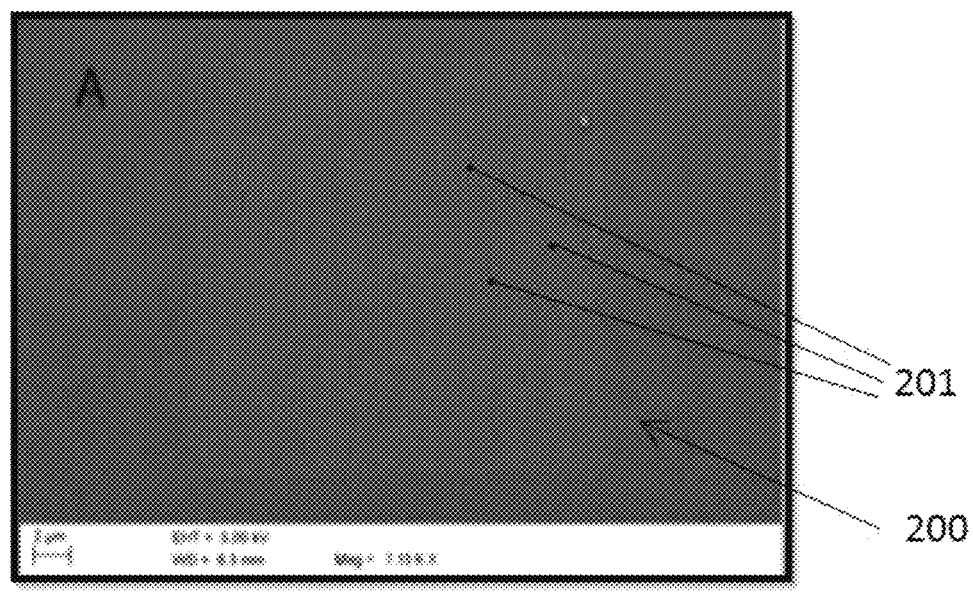
Figure 3:
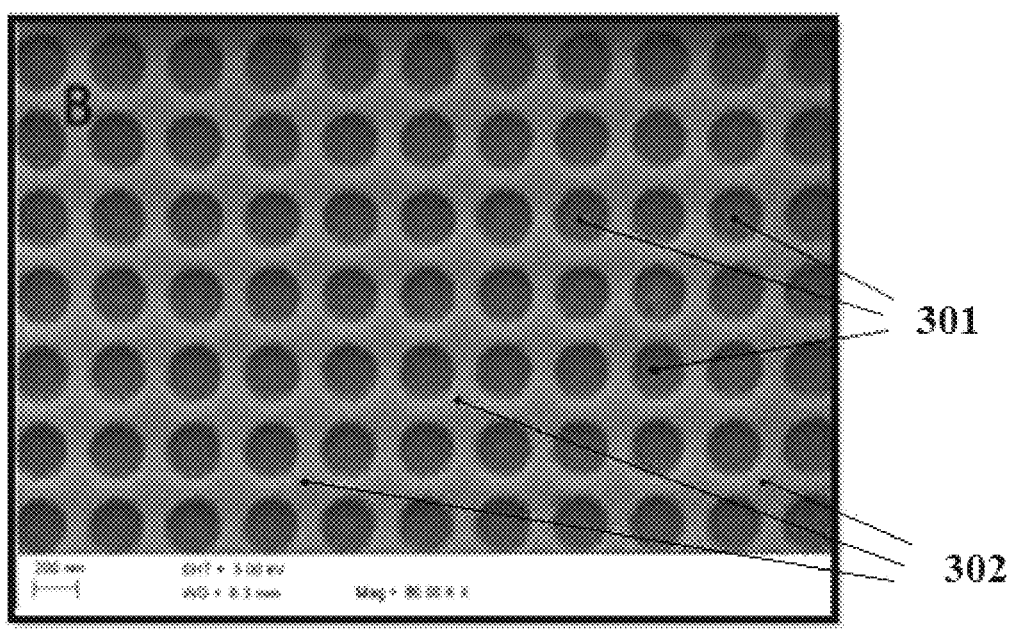

Referring to FIG. 1, FIG. 2 and FIG. 3 of the drawings, the phenomena upon which attributes of the present invention are exemplified and described. The present invention relates to application of optical diffraction properties and resultant interference in array of nanometer sized periodic structure with equally spacing, P 102, which is defined as the period as depicted and illustrated in FIG. 1 with cross-sectional view of an array of nano-holes or nano-dots at solid state material-to-air or in examples of the invention diamond-to-air interface on the facet surface of the exemplified mark. Again, this figure show a regular array formation with a constant period P of equal spacing, which is for explanatory purposes, and is not a limitation of the present invention.

As will be noted, the cross-sectional view of nano-holes or nano-dots may be interchangeable depending on the aspect ratio between top interface 101 as an interface outer surface and bottom interface 105 as an inner interface surface. The distance, h 103, between top interface 101 and bottom interface 105 between a solid state material such as gemstone or diamond to air is defined as the holes depth or dot height.

As will be understood by those skilled in the art, the sidewall 104 of nano-holes or nano-dots is not restricted to be a straight wall to be perpendicular to top interface 101 as the outer interface surface or bottom interface 105 as an inner interface surface, but may vary in inclination, geometry or shape to the extent such variance does not alter the functional aspects of the invention as described.

As will be appreciated by those skilled in the art, investigation of the dimensional and structural information of nano-structure directly under a conventional optical microscope is complex due to Rayleigh Criterion in optical limit.

Utilizing SEM (scanning electron microscope) techniques, the nano-fabricated structures may be viewed and measured under magnification of, for example 7,150× as shown in FIG. 2, and by a magnification of 80,000× FIG. 3) respectively.

In FIG. 2, by way of explanation as to the phenomena of attributes of the invention, it is shown that a regular and symmetry array 200 of nano-holes 201 are clearly viewed under 80,000 times magnified showing that nano-holes having a diameter of around 180 nm and period of around 300 nm while the lighter region 302 is considered as top interface 101 as an outer interface surface and the darkened circle 301 are considered as bottom interface 105 as an inner interface surface in FIG. 3, whereby the top interface 101 and bottom interface 105 are defined with reference to FIG. 1.

Figure 4A:
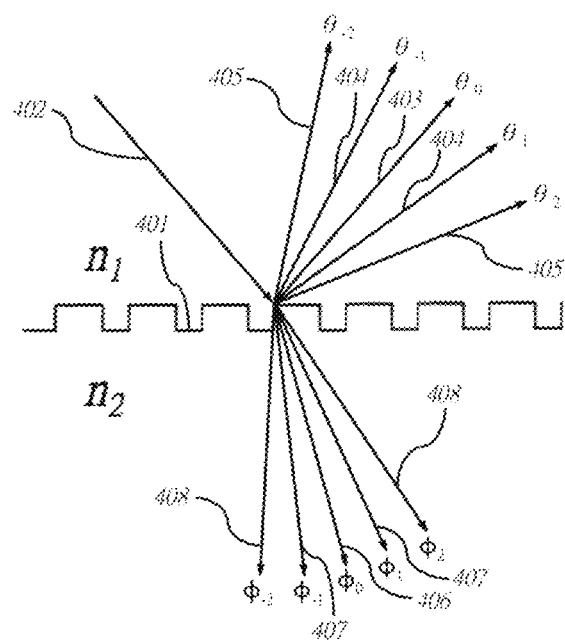
FIG. 4A is a schematic representation of a monochromatic light ray incident upon an array of nano-holes or nano-dots at a gemstone-to-air or diamond-to-air interface.

FIG. 4A illustrates the effect of a diffraction occurring at a nanometer sized periodic structure at the interface 401 between air-to-gemstone or air-to-diamond interface, where $n_1$ represents refractive index of the media of air while $n_2$ represents refractive index of the media of the solid state material or air. The incident monochromatic light ray 402 results in numerous different reflected rays 403 to 405 of variation in intensity resulting in local maxim due to interference being induced, with $\theta_n$ deviated from normal axis, and transmitted rays 403 to 405 with $\varphi_n$, deviated from normal axis where n=−2, −1, 0, 1 or 2 for corresponding diffractive orders and thus corresponding local maxima.

A viewing point set to be normal to the top facet of gemstone or diamond in an example, instead of 0th order of diffractive light 403 in the medium of air, the −+/−1st 404 and +/−2nd 405 order of reflected rays, may be employed in achieving the present invention on a gemstone or diamond or other solid state material.

Figure 10C:
FIG. 10C is a photographic representation of a further example of a gemstone facet surface marking in accordance with the present invention having a lattice of entities in a non-uniform and non-periodic arrangement, viewed at an optical axis normal to the facet with normal white light (up) as an Off-state.
Figure 11:
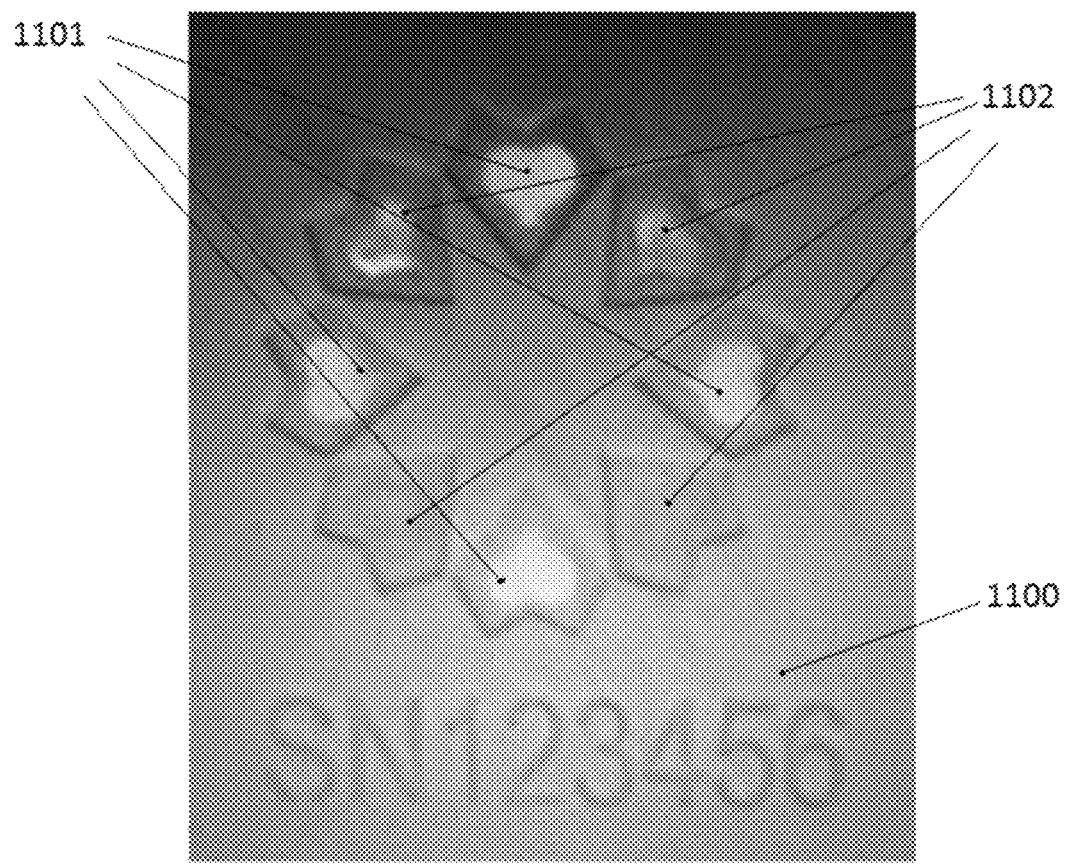

At this point, the −1st order of diffractive ray 404 is employed in calculations as shown in FIG. 4B to FIG. 9 and experimental results as shown in FIG. 10A, FIG. 10B and FIG. 11, whereby embodiments of the present invention are depicted in FIG. 10A, FIG. 10B and FIG. 11 and described further below. However as will be understood by those skilled in the art, other viewing points at alternate viewing may alternatively be utilised, without departing from the present invention.

Figure 4B:
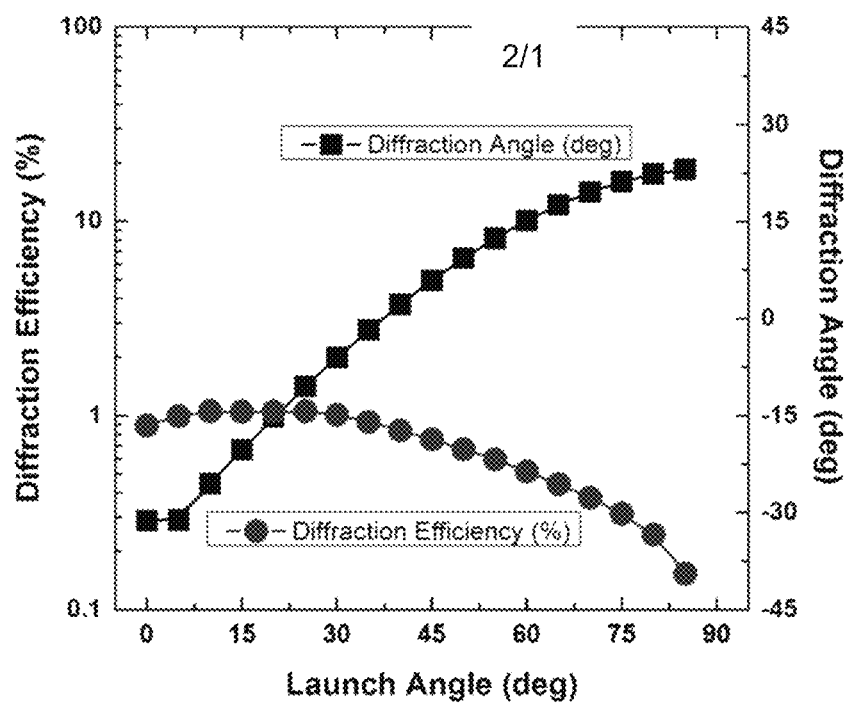
FIG. 4B shows a graph of a calculated diffraction angle and diffraction efficiency of a monochromatic light against its incident launch angle on an array of nano-holes or nano-dots at gemstone-to-air or diamond-to-air interface.

Referring to FIG. 4B, for fixed period, p 102 defined with reference to FIG. 1, of a lattice of nano-holes or nano-dots and fixed wavelength of monochromatic incident light, the diffraction efficiency and the diffraction angle of the −1th order of diffractive ray 404 are calculated by analytically solving Maxwell's equations into infinitely algebra equations which then high order terms are cut and numerically solved with finite accuracy convergence and the plot is demonstrated.

In this example, the desired diffraction angle of −1st order 404 should zero degrees from normal axis of the array of nano-holes or nano-dots if the reflected light is view normally when the incident launch angle of monochromatic light is at around 36 degrees as the diffraction efficiency is around 0.8% of incident monochromatic light intensity as well.

Figure 5:
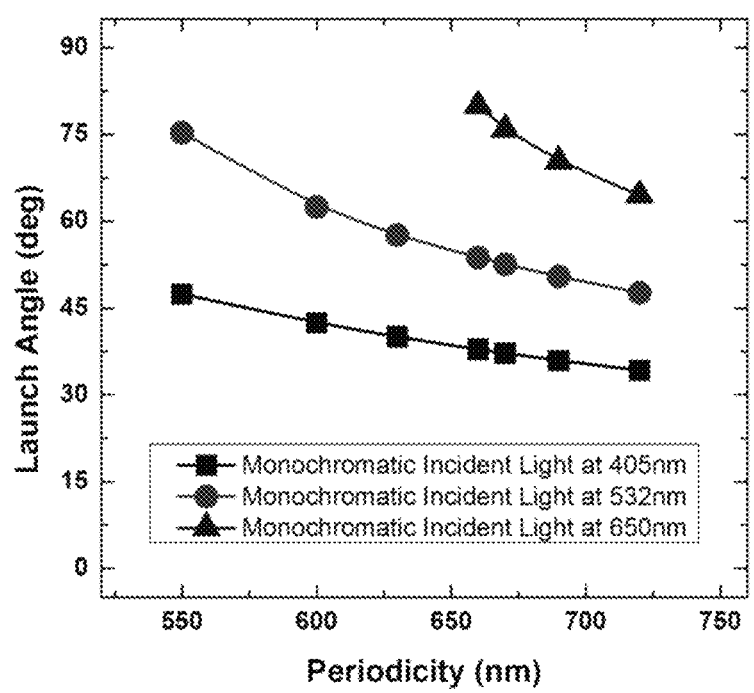

As the viewing angle of −1st diffractive order light 404 is fixed normal to the topfacet of gemstone or diamond, then the launch angle of incident light 402 is calculated that it highly depends on wavelength of monochromatic incident light 402, and also the periodicity of an array of nano-holes or nano-dots at the gemstone-to-air or diamond-to-air interface where wavelengths of 405 nm (visual blue colour), 532 nm (visual green colour) and 650 nm (visual red colour) are applied in this calculation with results as depicted in FIG. 5.

Figure 6:
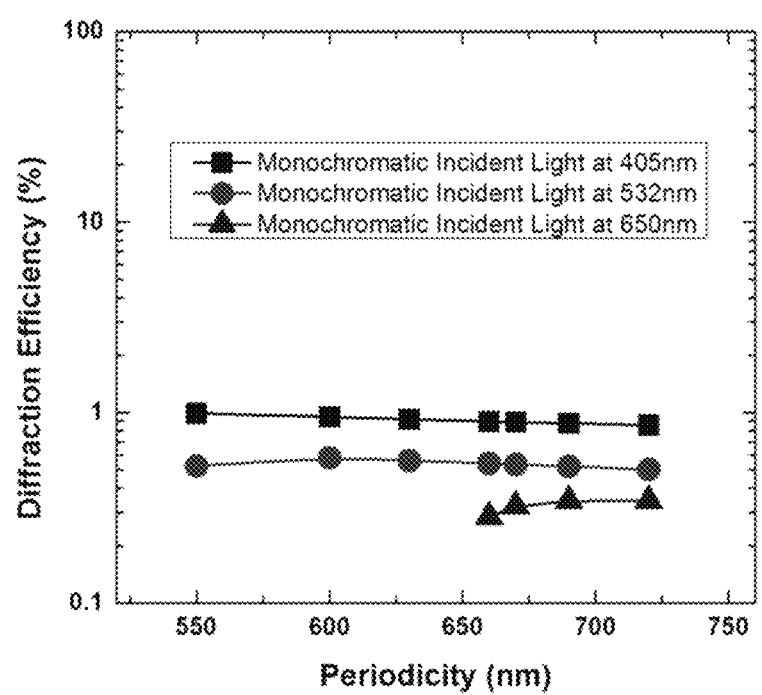

Referring to FIG. 6, the dependency of the diffraction efficiency for monochromatic incident light 402 having different wavelengths on periodicity of an array of nano-holes or nano-dots defined with reference to FIG. 4 is evaluated and plotted.

The results demonstrate that shorter wavelengths of monochromatic incident light 402 may provide enhanced diffraction efficiency by being at least two times stronger for 405 nm blue monochromatic incident light comparing to 650 nm red monochromatic incident light calculated at same period 102 defined with reference to FIG. 1 of nano-structure.

Figure 7:
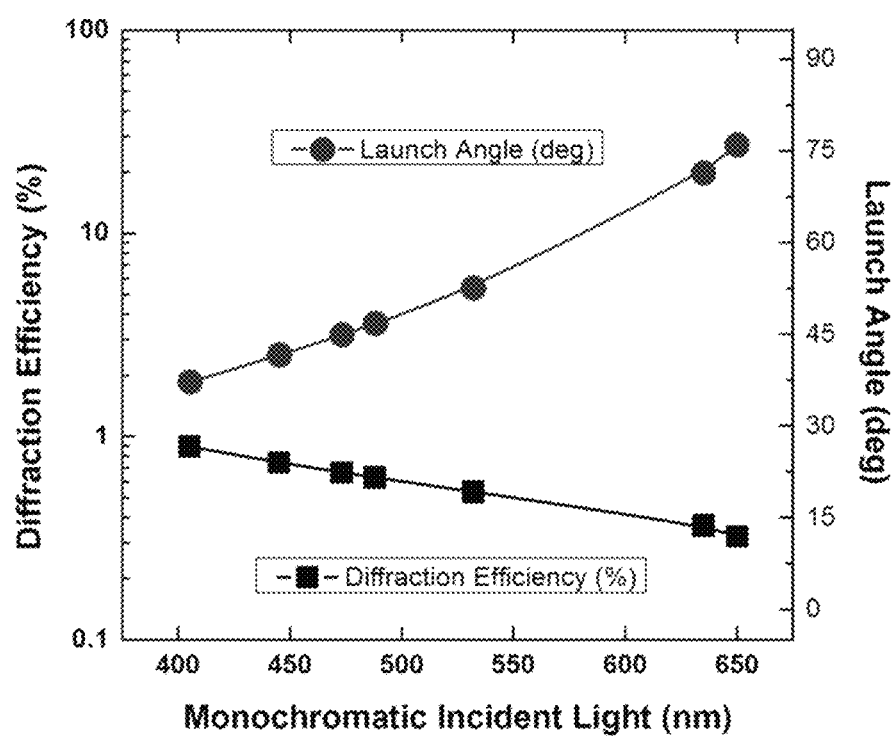

Referring to FIG. 7, it is shown that alternatively, by fixing the period 102 defined with reference to FIG. 1 of a lattice of nano-holes or nano-dots, the diffraction efficiency and incident launch angle for monochromatic incident light 402 defined with reference to FIG. 4 depends on wavelength of monochromatic incident light.

By evaluation it is demonstrated that the shorter wavelength of monochromatic incident light, the greater the diffraction efficiency but less incident launch angle.

Figure 8:
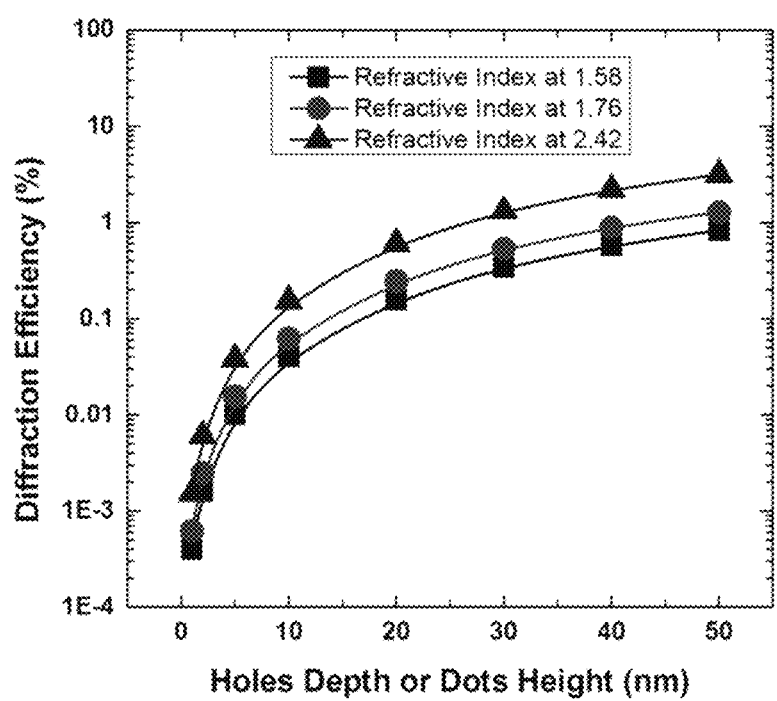

Referring to FIG. 8, another key parameter which may determine diffraction efficiency is physical depth 103 as defined and described with reference to FIG. 1 of an array of nano-holes or nano-dots at gemstone-to-air interface, where the refractive index of the gemstone or diamond plays an important as well. As demonstrated, the diffraction efficiency increases dramatically with an order of $10^3$ when the depth 103 of nano-holes or nano-dots changes from 1 nm to 50 nm, while there is approximately an 8 times enhancement when the refractive index of gemstone has 0.84 changes in value.

Figure 9:
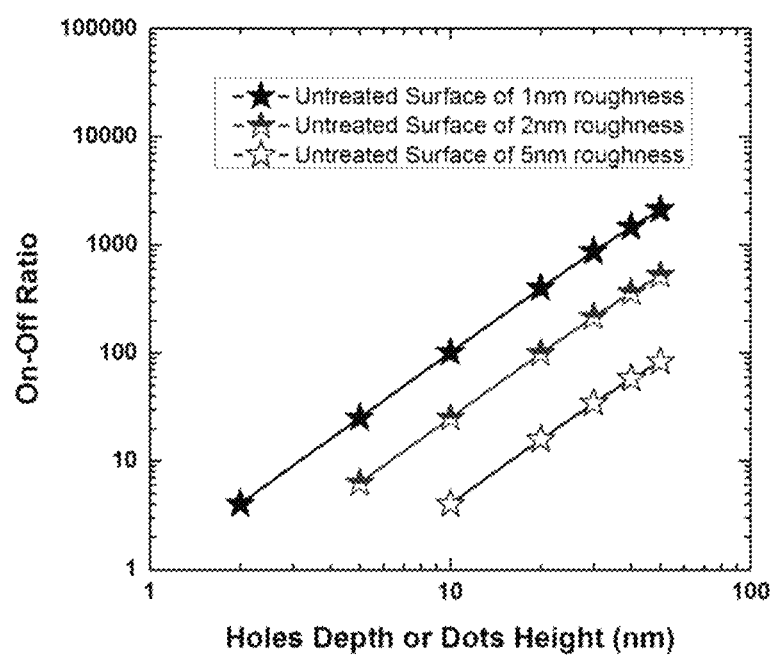

Referring to FIG. 9 and in the present invention and for explanatory purposes, the ratio of the reflected light intensity due to diffraction from the interference that is induced by the array of nano-holes or nano-dots to that of the background area, is termed On-Off Ratio contrast.

With optimization of above calculated results with respect to the present examples, the preferable calculated result of On-Off Ratio contrast of the concerned mark from the surrounding untreated surface roughness against physical depth of an array of nano-holes or nano-dots at gemstone-to-air interface, provides up to a value of $10^3$ contrast different.

However, as will be appreciated by those skilled in the art, the untreated surface roughness of the facet for marking is a detrimental factor for final On-Off Ratio of a particular colour mark when illuminated by monochromatic incident light 402, where the roughened surface does perform so as to scatter monochromatic incident light 402 defined with reference to FIG. 4, and may interfere with the observation of the concerned mark and hence may reduce the On-Off Ratio contrast.

Referring to FIG. 10A and FIG. 10B there is shown an exemplary magnified photographic representation of an example of the present invention, whereby there is shown a gemstone facet surface 1000 having an identifiable mark 1001 in accordance with the present invention, whereby the identifiable mark is provided on sapphire. The identifiable mark 1001 has been provided to the gemstone facet surface 1000 as a lattice of a plurality of discrete nanometer sized recessed or protruded entities in a lattice of a non-periodic and irregular structure. The entities are arranged within a predefined region of said facet in a predetermined arrangement in relation to each other, in accordance with the invention.

As shown in FIG. 10A, the representation depicts the gemstone facet surface 1000 with the identifiable mark 1001 in an Off-state, whereby normal white light is applied to the monochromatic incident light and has been applied to the gemstone facet surface 1000 when viewed at a normal optical axis to the gemstone facet surface 1000.

By contrast, as shown in FIG. 10B, the representation depicts the gemstone facet surface 1000 whereby normal white light plus intense green monochromatic light (532 nm) are applied simultaneously, and the identifiable mark 1001 is depicted in an On-state with significantly increased and enhanced brightness. As is depicted in FIG. 10A, when the identifiable mark 1001 is in the On-state, when reproduced in a grey-scale format, the identifiable mark 1001 in its On-state is depicted as a darkened portion with respect to the gemstone facet surface 1000.

Figure 10D:
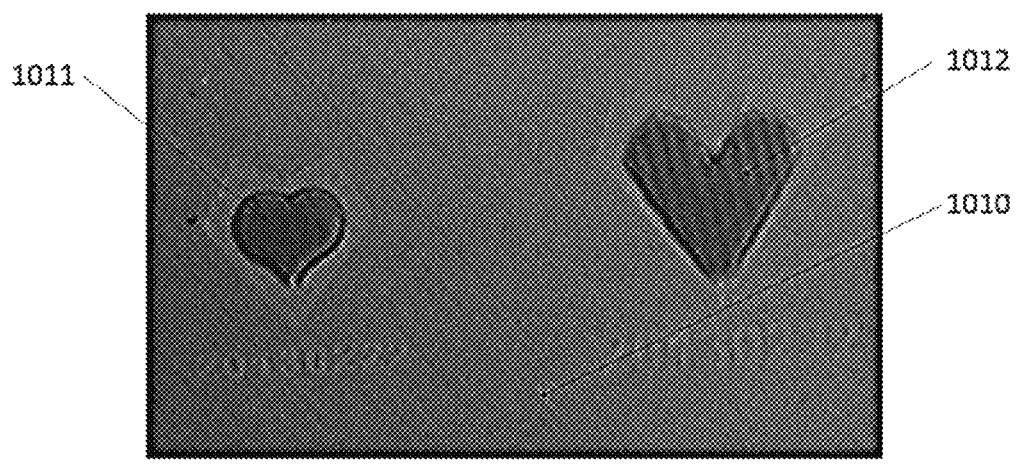
FIG. 10D depicts the gemstone facet surface of the gemstone facet surface of FIG. 10C with normal white light plus intense red monochromatic light simultaneously (bottom) an On-state, in accordance with the present invention.

Referring to FIG. 10C and FIG. 10D, there is shown an exemplary magnified photographic representation of a further example of the present invention, whereby there is shown a gemstone facet surface 1010 having two identifiable marks 1011 and 1012 in accordance with the present invention, whereby the identifiable marks are provided on sapphire. The identifiable marks 1011 and 1012 have been provided to the gemstone facet surface 1010 as a lattice of a plurality of discrete nanometer sized recessed or protruded entities of a non-periodicity and irregular structure. The entities are arranged within a predefined region of said facet in a predetermined arrangement in relation to each other, in accordance with the invention.

As shown in FIG. 10C, the gemstone facet surface 1010 with the identifiable marks 1011 and 1012 is in an Off-state, whereby normal white light is applied to the monochromatic incident light and has been applied to the gemstone facet surface 1010 when viewed at a normal optical axis to the gemstone facet surface 1010.

By contrast, as shown in FIG. 10D, the representation depicts the gemstone facet surface 1010 whereby normal white light plus intense red monochromatic light (650 nm) are applied simultaneously, and the identifiable marks 1011 and 1012 are depicted in an On-state with significantly increased and enhanced brightness. As is depicted, when the identifiable mark 1011 and 1012 are in the On-state, and when reproduced in a grey-scale format, the identifiable marks 1011 and 1012 in their On-state are depicted as darkened portions with respect to the gemstone facet surface 1010.

As depicted in FIG. 10D, the image demonstrates that two separate colour marks 1011 and 1012 can be lighted up as being in an On-state simultaneously.

As shown in both FIG. 10B and FIG. 10D, there is shown a manifestation of high On-Off Ratio contract after monochromatic light incident on the concerned marks 1001, and 1011 and 1012 respectively on sapphire surface 1000 and 1010 respectively. Also shown are obvious polished lines which may be considered as serious surface roughness and scatter as well, and where the concerned mark may be designed so as to have any arbitrary shapes or characters.

Referring to FIG. 11, there is depicted a magnified photographic representation of an example of the present invention. In the present example, there is shown a gemstone facet surface 1100 having a plurality of first identifiable marks 1101 and a plurality of second identifiable marks 1102.

The plurality of first identifiable marks 1101 is formed by a lattice of a plurality of discrete nanometer sized recessed or protruded entities of a non-periodicity and irregular structure, and the plurality of second identifiable marks 1102 is formed by a lattice of a plurality of discrete nanometer sized recessed or protruded entities of a non-periodicity and irregular structure, in accordance with the present invention.

As is shown, upon application of normal white light plus intense green monochromatic light (532 nm) and plus intense red monochromatic light (650 nm), the plurality of first marks 1101 and the plurality of second marks 1102 are in an On-state, with significantly increased and enhanced brightness, with a composite mark being provided with two distinct and different colours.

As is depicted in FIG. 11, when the plurality of first marks 1101 and the plurality of second marks 1102 are in the On-state, and when reproduced in a grey-scale format, the identifiable marks 1011 and 1012 in their On-state, these are depicted as darkened portions with respect to the gemstone facet surface 1110.

Advantageous attributes of the invention as demonstrated by the example of the invention of FIG. 11, by application of above calculated and experimental results, a multiple colour mark may be provided and viewed by appropriate control of incident angle of light, and the parameters of the entities and depth thereof of a lattice of nano-holes or nano-dots at gemstone-to-air or diamond-to-air interface. As a result, a brand or quality mark may be provided, which may also hold aesthetic appeal. Furthermore, for security purposes, such a mark may also, in relevant embodiments, provide a complex mark only viewable with known light and viewing parameters, thus providing a mark which is unique to a particular article to which it is applied.

Figure 12A:
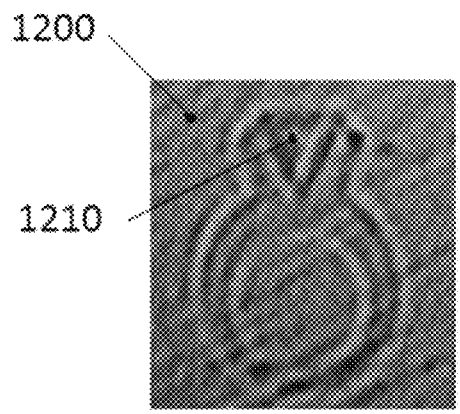
FIG. 12A is a photographic representation of an example of the present invention, depicted a gemstone facet surface mark at an optical axis normal to the facet with normal white light plus intense red monochromatic light simultaneously (bottom) as On-state.
Figure 12B:
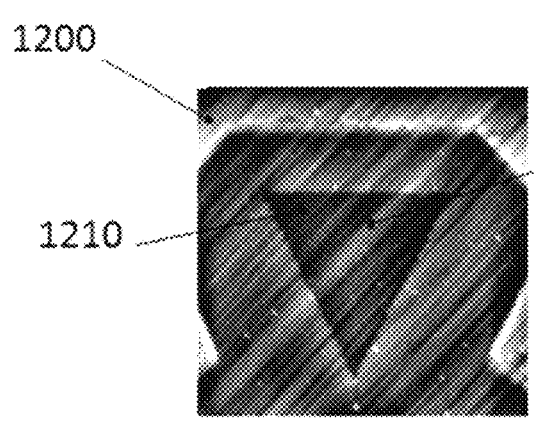
FIG. 12B is an Atomic Force Microscope (AFM) scan result showing the topography of a triangle colour mark according to the present invention as shown in FIG. 12A.
Figure 12C:
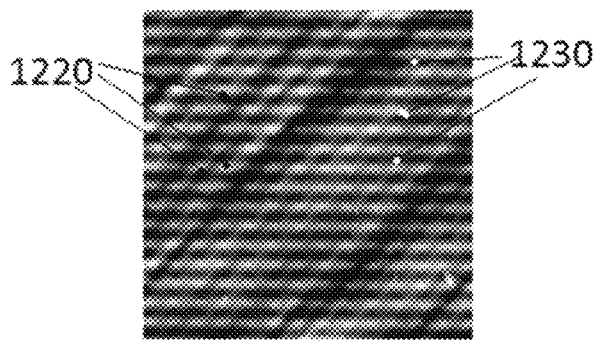
Figure 12D:
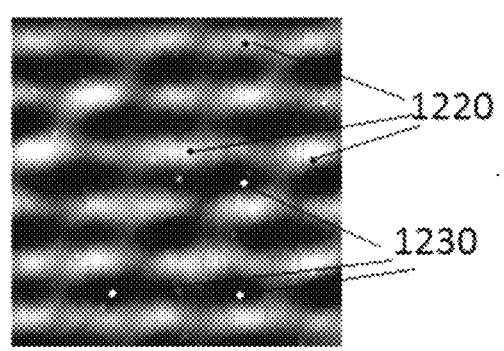
FIG. 12D is a further detailed AFM scan of the ROI of FIG. 12C showing the lattice of irregular/non-periodic spaced entities with arbitrary spacing and shapes according to the present invention.

Referring to FIGS. 12A to 12D, there is further illustrated the lattice structure of nano-sized entities according to the present invention in a non-uniform and non-periodic arrangement, whereby FIGS. 12B to 12D are microscopy representations utilising Atomic Force Microscopy (AFM) of the mark as depicted in FIG. 12A in accordance with the present invention.

FIG. 12A is a photographic representation of a gemstone facet surface 1200 having a mark 1210 applied thereto according to the present invention when viewed at an optical axis normal to the surface of the facet 1200 with normal white light plus intense red monochromatic light simultaneously (bottom) as an On-state observed by optical microscope, with the mark 1210 depicted as a darkened portion with respect to the gemstone facet surface 1200, when reproduced in grey scale.

From a lowest magnification and resolution of AFM of the marking 1210 of FIG. 12A as shown in FIG. 12B, the array of nano-sized entities 1220 are shown at a magnification using AFM at a 50 µm×50 µm magnification provide an initial appearance at this magnification to be relatively regularly arranged and having relatively similar size.

However, as is shown and depicted by FIG. 12C, when an increase in effective magnification for viewing by reducing scan area at a magnification using AFM at a 15 µm×15 µm image ROI (Region of Interest) at middle of the concerned triangle colour mark shown in FIG. 12A, it is depicted and demonstrated there exist distinct breaks 1230 in continuity of the entities 1220 in all directions along the marked region due to nano-sized entities 1220 with arbitrary spacing and shapes, and as such the distribution of the entities is irregular, non-periodic and non-symmetric.

Such an irregular, non-periodic and non-symmetric arrangement and distribution of the entities 1220 in accordance with the present invention is further demonstrated and exemplified as depicted in FIG. 12D, whereby the magnification using AFM is at a 3.5 µm×3.5 µm image ROI (Region of Interest) at middle of the concerned triangle colour mark 1210 shown in FIG. 12A.

Referring to FIGS. 13A, 13B and 13C, there are shown AFM scans of an example of a mark 1300 applied to an article in accordance with the present invention, whereby the entities 1310 which form the mark 1300 are arbitrary shaped and irregular/non-periodic spaced entities 1310.

Referring to FIG. 13A, there is shown a detailed AFM scan depicted the a lattice of irregular/non-periodic spaced entities 1310 with arbitrary spacing and shapes along the X-Y axis as shown at the left-upper corner, providing an example of the mark 1300 applied to an article in accordance with the present invention.

Referring FIG. 13B, there is shown colour transformation of the scan of FIG. 13A, with rainbow colour range from Blue to Red which is representative of topographic change from lowest depth (Blue) 1320 as represented by the darker portions when reproduced in grey-scale, to the top surface (Red) 1330 as represented by the lighter portions when reproduced in grey-scale, as well as clearly showing the construction and arrangement of arbitrary shapes having irregular/non-periodic spaced entities 1310 in both X-axis and Y-axis, without periodicity.

Referring to FIG. 13C, there is shown a 3D contour plot of the mark of FIG. 13B, demonstrating the change of topography due to arbitrary shaped and irregular/non-periodic spaced entities. There is shown variation of the height/depth from lowest depth (Blue) as represented by the darker portions when reproduced in grey-scale to the top surface (Red) as represented by the darker portions when reproduced in grey-scale, with range of 30 nm in this case of the nano-sized entities 1330.

As is shown and demonstrated by FIGS. 13A, 13B and 13C, the nano-sized entities which form the mark 1300 have size, shape, spacing and depth which are dynamic in 3-dimensions, demonstrating that the nano-sized entities 1330 are arranged in irregular/non-periodic lattice.

In the example of the present invention, the fabrication of discrete entities 1330 having arbitrary shape and irregular/non-periodic spacing is achieved by controlling the focused ion beam path as a function of time and positions when the focused ion beam remains.

It will be understood by those skilled in the art that other nano-fabrication methods may be used in accordance with the invention, including focused ion beam, a deep UV (ultraviolet) laser beam, wet chemical etching, ion plasma etching, different aspect ratio of shadow mask for plasma etch process or the like, or any combination thereof, without departing from the scope of the invention.

Figure 14:
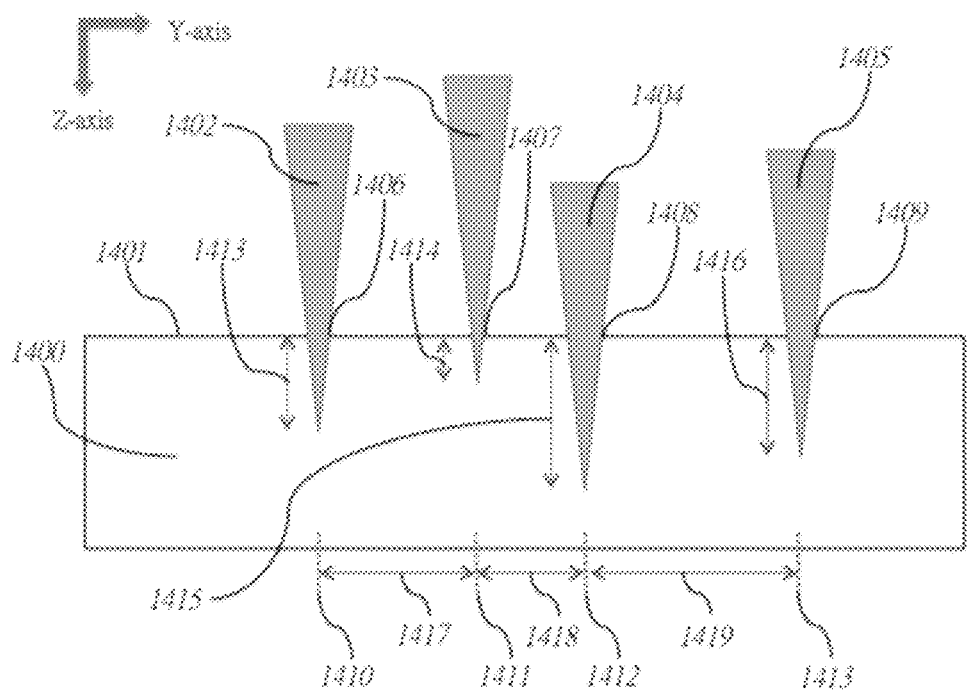

Referring to FIG. 14, there is shown is a schematic representation of a focused ion beam passing across the top surface of gemstone facet to fabricate entities along the Y-axis with various spacings and Z-axis having various depths.

The focused ion beam is controlled to irradiate on top surface 1401 of an article which in this representation may be a gemstone facet 1400 along the Y-axis from left-to-right against time is illustrated as ion beams 1402, 1403, 1404 and 1405 at positions 1410, 1411, 1412 and 1413 respectively whereby the beam conditions such as accelerating voltage, probe current and dose and the like are independent of time.

Again, as will be understood by those skilled in the art, other nano-fabrication methods may be used in accordance with the invention, including focused ion beam, a deep UV (ultraviolet) laser beam, wet chemical etching, ion plasma etching, different aspect ratio of shadow mask for plasma etch process or the like, or any combination thereof, without departing from the scope of the invention.

In the present exemplary schematic representation, the positions 1410, 1411, 1412 and 1413 may be generated as:

Ion beam (*i*) position in *Y*-axis=Desired General Spacing (nm)+Allowed Variation Range (nm)× Random Generator (−1 to 1)   (i)

wherein:
i is the count of ion beam irradiating on the surface 1401 of gemstone 1400 facet,
Desired General Spacing may be in range of 200 nm to 900 nm, and
Allowed Variation Range may be in range of 10% to 50% of Desired General Spacing.

In the present example, the arbitrary shape, in depth/height and X-Y dimensions of discrete entities are controlled by varying the dwell time and the focusing position of ion beam along Z-axis 1413, 1414, 1415 and 1416 at each moment of time that the ion beam remains at a position.

The dwell time may be generated as:

Ion beam (*i*) Dwell Time=Desired General Dwell Time (μs)+Allowed Variation Range (μs)×Random Generator (−1 to 1)   (ii)

wherein
Desired General Dwell Time may be in range of 0.1 μs to 100 μs, and
Allowed Variation Range may be in range of 10% to 50% of Desired General Dwell Time.

The depth positions 1413, 1414, 1415 and 1416 where the ion beam is focused at, relative to the top surface 1401 of gemstone 1400 facet, may be generated as:

Ion beam (*i*) position in *Z*-axis=Desired General Depth (nm)+Allowed Variation Range (nm)× Random Generator (0 to 1)   (iii)

wherein
Desired General Depth may be in range of 0 nm to 100 nm, and
Allowed Variation Range may be in range of 10% to 50% of Desired General Spacing.

The generated parameters of ion beam position in Y-axis and Z-axis and Dwell time may be provided as a path list for the focused ion beam to follow and irradiate on the top surface 1401 of a solid state material such as a gemstone 1400 facet.

As a result, at each site of focused ion beam irradiation, the interaction cross-section 1406, 1407, 1408 and 1409 and interaction volume would be independent in fabricating each entity from others. Also, the spacings 1417, 1418 and 1419 between entities vary along the X-Y plane as shown in FIG. 13 as a result of a non-symmetric lattice with irregular/non-periodic spaced and shaped entities.

The present invention provides a mark and method of formation thereof, which may be applied to a facet of a gemstone or other solid state material, which does not detract from the optical properties of the gemstone to which it is applied.

Such markings may be for grading purposes, security purposes, denote origin of the gemstone, ownership or the like.

As will be appreciated by those skilled in the art, different wavelengths of light allow for multiple colour aspects to be applied to the gemstone, so as to provide any requisite representation.

As will also be appreciated by those skilled in the art, numerous different geometric attributes may be applied to the mark, such as regular or irregular shaped holes, dots, disks, pillars or the like, circular array, spiral array, square array, triangular array, hexagonal array, fractal array, multiple period, or a combination thereof.

The following highlights the advantages of the present invention, whereby the present invention provides numerous advantages over those of the prior art, which allows benefits to be obtained which cannot be achieved by the prior art.

The present invention, allows provision of a marking structure which is not by way of grooves and which does not include or require periodicity, but rather a lattice of discrete entities in a non-periodic and non-symmetric arrangement, which allows more complex marking as well as more than one colour of light to be reflected readily from the same single marking.

Furthermore, the use of the present invention allows for a marking structure for which the size, shape, geometry and spacing may be varied, thus allowing for more complex marking as well as a plurality of colour components to be viewable.

Thus, advantages of examples or embodiments according to the present invention may include those as follows:
(i) more complex markings,
(ii) more than one wavelength of light reflected, and
(iii) less manufacturing steps, thus providing a more efficient marking process.

Embodiments of the present invention, for example by use of focused ion beam to provide the marking, obviates the necessity of a step which requires use of an oxidising agent, by contrast to the prior art.

Obviating such a step provides for obviating or removal of numerous adverse production, occupational health and safety and environmental issues to obviated, including obviating the requirement for a typical chemical used in the prior art, molten potassium nitrate, which include:
(i) lower cost,
(ii) no health risk exposure to fumes of such a chemical, thus increasing occupational health and safety,
(iii) no explosion risk from potassium nitrate,
(iv) no disposal related risks (OHS) and processing of was molten potassium nitrate, again increasing occupational health and safety, and
(v) no costs associated with disposal costs for processing of molten potassium nitrate.

The mark of the present invention may only be viewed under suitable magnification of microscope objective from a predetermined direction, preferably the normal direction, of a solid state material including a marked facet of a gemstone or diamond by incident monochromatic light at specified angle, where the incident monochromatic or panchromatic light is intensive, however greater image contrast may be attained if the incident light is collimated and coherent.

The present invention is distinguished from those techniques of the prior art, such as that of U.S. Pat. No. 6,391,215, whereby the light entering the microscope objective is any diffractive light other than 0th order or direct reflecting light.

Further, the present invention is distinguished form others in the art in applying properties of diffractive optics in the field of gemstone markings, whereby the prior art is directed to enhancing the optical characteristics of a gemstone or diamond (U.S. Pat. No. 8,033,136 B2) and decorative and ornamental of gemstone or diamond (U.S. Pat. No. 8,233, 218 B1) under normal light.

By contrast the mark of the present invention utilises a strong On-Off contrast by diffraction orders, thus resulting in variation in intensity due to induced interference, from an untreated surface to show the information regarding identification of a solid state material including a gemstone, such as by marking an invisible serial number or as an invisible brand or quality mark.

What is claimed is:

1. An identifiable mark on a portion of a polished facet of a surface of an article and being identifiable by an optical magnifying viewing device, said identifiable mark comprising:
   a nano-structure formed by a two-dimensional or a three-dimensional lattice of a plurality of discrete nanometer sized recessed or protruded entities, wherein said entities are arranged within a predefined region of said polished facet in a predetermined arrangement in relation to each other, and such that an outer interface surface between the facet of the article and air is formed and an inner interface surface between the facet of the article and air is formed;
   wherein said predetermined arrangement of said entities is a non-uniform and non-periodic arrangement, and the predetermined arrangement of the non-uniform and non-periodic arrangement of said entities provides a change of topography of said lattice due to arbitrary shaped and non-uniform and non-periodic spaced entities, and wherein said entities are sized and shaped so as to cause optical scattering upon reflection of incident light, and the distance from the inner interface surface to the outer interface surface is greater than the amplitude of the non-marked portion of said polished facet;
   such that upon reflection of incident light said incident light having one or more predetermined wavelengths by said lattice of said entities having said predetermined arrangement at a predetermined angle of incidence to said lattice, interference due to scattering of light from said lattice is induced, such that reflected light has a variation in intensity providing one or more local maxima of one or more wavelengths; and
   wherein said mark is invisible to the naked eye and is invisible when utilizing an optical magnifying viewing device under normal light conditions, and wherein said mark is identifiable by way of the optical magnifying viewing device inclined at a requisite viewing angle under incident light having said one or more predetermined wavelengths such that a local maxima is detected and wherein said mark has significantly increased and enhanced brightness.

2. The identifiable mark of claim 1, wherein said entities of said lattice are spaced apart in the range of from 10 nm to 900 nm, the discrete entities have a maximum lateral dimension in the range of from 1 nm to 899 nm, and the normal distance between the outer interface surface and the inner interface surface is in the range of from 1 nm to 200 nm.

3. The identifiable mark of claim 1, wherein said two-dimensional or a three-dimensional lattice provides at least one identifiable mark having two or more colour features viewable by way of said optical magnification viewing device.

4. The identifiable mark of claim 1, wherein said non-marked portion of said facet has an average surface roughness less than about 1 nm.

5. The identifiable mark of claim 1, wherein said variation in intensity is distinguishable by human eye or an optical camera from any reflected signal from the non-marked portion of said facet.

6. The identifiable mark of claim 1, wherein the recessed or protruded entities of said two-dimensional or a three-dimensional lattice are either regular or irregular shaped holes, dots, disks, pillars or the like, and may be provided as a circular arranged lattice, spiral arranged lattice, square arranged lattice, triangular arranged lattice, hexagonal arranged lattice, fractal arranged lattice, or multiple combination thereof.

7. The article having thereon an identifiable mark of claim 1.

8. The article of claim 7, wherein said article is a gemstone, is selected from the group including Diamond, Ruby, Sapphire, Emerald, Pearl, Jade, Tourmaline or the like.

9. The article of claim 7, wherein said lattice is provided in a region of about 400 µm×400 µm on the polished facet.

10. The method of viewing an identifiable mark on an article as recited in claim 7, further including the steps of:
    providing incident light having one or more predetermined wavelengths at a predetermined angle of incidence to the identifiable mark; and
    viewing said identifiable mark at said requisite viewing angle by way of an optical viewing device such that a local maxima is detected.

11. A method of providing an identifiable mark on a portion of a polished facet of a surface of an article and being identifiable by an optical magnifying viewing device, said method including the steps of:
    forming a nano-structure of a two-dimensional or a three-dimensional lattice of a plurality of discrete nanometer sized recessed or protruded entities on a portion of a facet of an article, wherein said entities are arranged within a predefined region of said facet in a predetermined arrangement in relation to each other, and such that an outer interface surface between the facet of the article and air is formed and an inner interface surface between the facet of the article and air is formed;
    wherein said predetermined arrangement of said entities is non-uniform and non-periodic arrangement and the predetermined arrangement of the non-uniform and non-periodic arrangement of said entities provides a change of topography of said lattice due to arbitrary shaped and non-uniform and non-periodic spaced entities, and wherein said entities are sized and shaped so as to cause optical scattering such that upon reflection of incident light, and the distance from the inner interface surface to the outer interface surface is greater than the amplitude of the non-marked portion of said polished facet;
    such that upon reflection of incident light having one or more predetermined wavelengths by said lattice of said entities having said predetermined arrangement at a predetermined angle of incidence to said lattice, interference due to scattering of light from said lattice is induced, such that reflected light has a variation in intensity providing one or more local maxima of one or more wavelengths; and
    wherein said mark is invisible to the naked eye and is invisible when utilizing an optical magnifying viewing device under normal light condition, and wherein said mark is identifiable by way of the optical magnifying viewing device inclined at a requisite viewing angle under incident light having said one or more predetermined wavelengths such that a local maxima is detected and wherein said mark has significantly increased and enhanced brightness.

12. The method of claim 11, wherein said two-dimensional or a three-dimensional lattice of nanometer sized discrete entities is formed from a nano-fabrication method, wherein said nano-fabrication method is a method including focused ion beam, a deep UV (ultraviolet) laser beam, wet chemical etching, ion plasma etching, different aspect ratio of shadow mask for plasma etch process or the like, or any combination thereof.

13. The method of claim 11, wherein said two-dimensional or a three-dimensional lattice is formed by a focused ion beam and by way of dynamic control variation of the spot size and dose of the focused ion beam.

14. The method of claim 11, wherein said article is a gemstone, and wherein the gemstone is selected from the group including Diamond, Ruby, Sapphire, Emerald, Pearl, Jade, Tourmaline or the like.

15. An article having an identifiable mark formed on a portion of a polished facet of a surface of the article, wherein the identifiable mark is formed according to the method of claim 11.

* * * * *